United States Patent
Liu

(10) Patent No.: US 11,459,364 B2
(45) Date of Patent: Oct. 4, 2022

(54) CALBINDIN AND BH3 DOMAIN CHIMERIC PROTEINS AND METHODS FOR USE

(71) Applicant: ProDa Biotech LLC, Marietta, GA (US)

(72) Inventor: Zhi-Ren Liu, Marietta, GA (US)

(73) Assignee: ProDa Biotech LLC, Marietta, GA (US)

( * ) Notice: Subject to any disclaimer, the term of this patent is extended or adjusted under 35 U.S.C. 154(b) by 62 days.

(21) Appl. No.: 15/124,024

(22) PCT Filed: Mar. 6, 2015

(86) PCT No.: PCT/US2015/019095
§ 371 (c)(1),
(2) Date: Sep. 6, 2016

(87) PCT Pub. No.: WO2015/134833
PCT Pub. Date: Sep. 11, 2015

(65) Prior Publication Data
US 2017/0226170 A1  Aug. 10, 2017

Related U.S. Application Data

(60) Provisional application No. 61/949,345, filed on Mar. 7, 2014.

(51) Int. Cl.
*C07K 19/00* (2006.01)
*C07K 14/47* (2006.01)
*A61K 47/55* (2017.01)
*A61K 47/60* (2017.01)
*A61K 47/54* (2017.01)
*A61K 31/282* (2006.01)
*A61K 38/17* (2006.01)
(Continued)

(52) U.S. Cl.
CPC ........ *C07K 14/4728* (2013.01); *A61K 31/282* (2013.01); *A61K 38/1738* (2013.01); *A61K 38/1761* (2013.01); *A61K 47/545* (2017.08); *A61K 47/551* (2017.08); *A61K 47/60* (2017.08); *A61K 49/0002* (2013.01); *C07K 14/47* (2013.01); *C07K 14/4747* (2013.01); *A61K 38/00* (2013.01); *C07K 2319/00* (2013.01)

(58) Field of Classification Search
None
See application file for complete search history.

(56) References Cited

PUBLICATIONS

Becker et al.. Characterization of the c-Jun N-Terminal Kinase-BimEL Signaling Pathway in Neuronal Apoptosis, J. Neurosci. 24(40):8762-8770, Oct. 2004.*

(Continued)

*Primary Examiner* — Claire Kaufman
(74) *Attorney, Agent, or Firm* — Greenberg Traurig LLP

(57) ABSTRACT

Therapeutic proteins for inducing apoptosis in cells and method for using such proteins are described. The protein, e.g., a chimeric protein, has a host peptide fused to a more stable BH3 domain peptide. The host peptide may be Calbindin D9k, a N-terminal or C-terminal half-domain of Calmodulin, Parvalbimin ("Pa"), an amino acid sequence variant thereof, or a modified variant thereof. The BH3 domain may be Bim, Bid, Bad, Bik, Bmf, Hrk, Puma, or Noxia. Moreover, various conjugates may be attached to the chimeric protein, including a folate and polyethylene glycol.

8 Claims, 12 Drawing Sheets

Specification includes a Sequence Listing.

(51) Int. Cl.
*A61K 49/00* (2006.01)
*A61K 38/00* (2006.01)

(56) References Cited

PUBLICATIONS

Antignani et al., A chimeric protein induces tumor cell apoptosis by delivering the human Bcl-2 family BH3-only protein bad, Biochem. 44:4074, 2005.*

Azar et al., GnRH-Bik/Bax/Bak chimeric proteins target and kill adenocarcinoma cells; the general use of pro-apoptotic proteins of the Bcl-2 family as novel killing components of targeting chimeric proteins, Apoptosis, 5:531-542, 2000.*

Delgado et al., The uses and properties of PEG-linked proteins, Criti. Rev. Therapeutic Drug Carriers and Systems, 9(3,4):294-304, 1992.*

* cited by examiner

SEQUENCE LISTING

```
<160> NUMBER OF SEQ ID NOS: 10

<210> SEQ ID NO 1
<211> LENGTH: 103
<212> TYPE: PRT
<213> ORGANISM: Artificial Sequence
<220> FEATURE:
<223> OTHER INFORMATION: Chimeric Variant of human protein and a variant
      of a BH3 domain

<400> SEQUENCE: 1

Glu Leu Met His His His His His Leu Glu Met Ser Thr Lys Lys
1               5                   10                  15

Ser Pro Glu Glu Leu Lys Arg Ile Phe Glu Lys Tyr Ala Ala Lys Glu
            20                  25                  30

Gly Asp Pro Asp Gln Leu Ser Lys Asp Glu Leu Lys Leu Leu Ile Gln
        35                  40                  45

Ala Glu Phe Pro Cys Leu Leu Lys Gly Pro Asn Thr Leu Asp Asp Leu
    50                  55                  60

Phe Gln Glu Leu Asp Lys Asn Gly Ala Gly Ala Val Ser Phe Glu Asp
65                  70                  75                  80

Met Arg Pro Glu Ile Trp Ile Ala Gln Glu Leu Arg Arg Ile Gly Asp
```

Glu Phe Asn Ala Tyr Tyr Ala
            100

<210> SEQ ID NO 2
<211> LENGTH: 102
<212> TYPE: PRT
<213> ORGANISM: Artificial Sequence
<220> FEATURE:
<223> OTHER INFORMATION: Chimeric Variant of human protein and a variant
      of a BH3 domain

<400> SEQUENCE: 2

Glu Leu Met His His His His His Leu Glu Met Ser Thr Lys Lys
1               5                   10                  15

Ser Pro Glu Glu Leu Lys Arg Ile Phe Glu Lys Tyr Ala Ala Lys Glu
            20                  25                  30

Gly Asp Pro Asp Gln Leu Ser Lys Asp Glu Leu Lys Leu Leu Ile Gln
        35                  40                  45

Ala Glu Phe Pro Cys Leu Leu Lys Gly Pro Asn Thr Leu Asp Asp Leu
    50                  55                  60

Phe Gln Glu Leu Asp Lys Asn Gly Ala Gly Ala Val Ser Phe Glu Glu
65                  70                  75                  80

Asp Ile Ile Arg Asn Ile Ala Arg His Leu Ala Gln Val Gly Asp Ser
                85                  90                  95

Met Asp Arg Ser Ile Trp
            100

<210> SEQ ID NO 3
<211> LENGTH: 102
<212> TYPE: PRT
<213> ORGANISM: Artificial Sequence
<220> FEATURE:
<223> OTHER INFORMATION: Chimeric Variant of human protein and a variant
      of a BH3 domain

<400> SEQUENCE: 3

Glu Leu Met His His His His His Leu Glu Met Ala Asp Gln Leu
1               5                   10                  15

Thr Glu Glu Gln Ile Ala Glu Phe Lys Glu Ala Phe Ser Leu Phe Asp
            20                  25                  30

Lys Asp Gly Asp Gly Thr Ile Thr Thr Lys Glu Leu Gly Thr Val Met
        35                  40                  45

Arg Ser Leu Gly Gln Asn Pro Thr Glu Cys Glu Leu Gln Asp Met Ile
    50                  55                  60

Asn Glu Val Asp Ala Ala Gly Asn Gly Thr Ile Ala Phe Pro Asp Met
65                  70                  75                  80

Arg Pro Glu Ile Trp Ile Ala Gln Glu Leu Arg Arg Ile Gly Asp Glu
                85                  90                  95

Phe Asn Ala Tyr Tyr Ala
            100

<210> SEQ ID NO 4
<211> LENGTH: 100
<212> TYPE: PRT
<213> ORGANISM: Artificial Sequence
<220> FEATURE:
<223> OTHER INFORMATION: Chimeric Variant of human protein and a variant
      of a BH3 domain

<400> SEQUENCE: 4

Glu Leu Met His His His His His Leu Glu Met Ala Asp Gln Leu
1               5                   10                  15

Thr Glu Glu Gln Ile Ala Glu Phe Lys Glu Ala Phe Ser Leu Phe Asp
                20                  25                  30

Lys Asp Gly Asp Gly Thr Ile Thr Thr Lys Glu Leu Gly Thr Val Met
            35                  40                  45

Arg Ser Leu Gly Gln Asn Pro Thr Glu Cys Glu Leu Gln Asp Met Ile
50                      55                  60

Asn Glu Val Asp Ala Ala Gly Asn Gly Thr Ile Ala Phe Pro Glu Asp
65                  70                  75                  80

Ile Ile Arg Asn Ile Ala Arg His Leu Ala Gln Val Gly Asp Ser Met
                85                  90                  95

Asp Arg Ser Ile
            100

<210> SEQ ID NO 5
<211> LENGTH: 101
<212> TYPE: PRT
<213> ORGANISM: Artificial Sequence
<220> FEATURE:
<223> OTHER INFORMATION: Chimeric Variant of human protein and a variant
      of a BH3 domain

<400> SEQUENCE: 5

Glu Leu Met His His His His His Leu Glu Met Ser Thr Lys Lys
1               5                   10                  15

Ser Pro Glu Glu Leu Lys Arg Ile Phe Glu Lys Tyr Ala Ala Lys Glu
                20                  25                  30

Gly Asp Pro Asp Gln Leu Ser Lys Asp Glu Leu Lys Leu Leu Ile Gln
            35                  40                  45

Ala Glu Phe Pro Cys Leu Leu Lys Gly Pro Asn Thr Leu Asp Asp Leu
50                      55                  60

Phe Gln Glu Leu Asp Lys Asn Gly Asp Gly Glu Val Ser Phe Glu Glu
65                  70                  75                  80

Phe Gln Val Leu Val Lys Lys Ile Ala Gln Glu Leu Arg Arg Ile Gly
                85                  90                  95

Asp Glu Phe Asn Ala
            100

<210> SEQ ID NO 6
<211> LENGTH: 86
<212> TYPE: PRT
<213> ORGANISM: Artificial Sequence
<220> FEATURE:
<223> OTHER INFORMATION: Chimeric Variant of human protein and a variant
      of a BH3 domain

<400> SEQUENCE: 6

His Met Ser Thr Lys Lys Ser Pro Glu Glu Leu Lys Arg Ile Phe Glu
1               5                   10                  15

Lys Tyr Ala Ala Lys Glu Gly Asp Pro Asp Gln Leu Ser Lys Asp Glu
                20                  25                  30

Leu Lys Leu Leu Ile Gln Ala Glu Phe Pro Cys Leu Leu Lys Gly Pro
            35                  40                  45

Asn Thr Leu Asp Asp Leu Phe Gln Glu Leu Asp Lys Asn Asn Leu Trp
        50                  55                  60

Ala Ala Gln Arg Tyr Gly Arg Glu Leu Arg Arg Met Ser Asp Glu Phe
65                  70                  75                  80

Val Asp Ser Phe Lys Lys
            85

<210> SEQ ID NO 7
<211> LENGTH: 86
<212> TYPE: PRT
<213> ORGANISM: Artificial Sequence
<220> FEATURE:
<223> OTHER INFORMATION: Chimeric Variant of human protein and a variant
      of a BH3 domain

<400> SEQUENCE: 7

His Met Ser Thr Lys Lys Ser Pro Glu Glu Leu Lys Arg Ile Phe Glu
1               5                   10                  15

Lys Tyr Ala Ala Lys Glu Gly Asp Pro Asp Gln Leu Ser Lys Asp Glu
                20                  25                  30

Leu Lys Leu Leu Ile Gln Ala Glu Phe Pro Cys Leu Leu Lys Gly Pro
            35                  40                  45

Asn Thr Leu Asp Asp Leu Phe Gln Glu Leu Asp Lys Asn Glu Glu Gln
        50                  55                  60

Trp Ala Arg Glu Ile Gly Ala Gln Leu Arg Arg Met Ala Asp Asp Leu
65                  70                  75                  80

Asn Ala Gln Tyr Glu Arg
            85

<210> SEQ ID NO 8
<211> LENGTH: 87
<212> TYPE: PRT
<213> ORGANISM: Artificial Sequence
<220> FEATURE:
<223> OTHER INFORMATION: Chimeric Variant of human protein and a variant
      of a BH3 domain

<400> SEQUENCE: 8

His Met Ser Thr Lys Lys Ser Pro Glu Glu Leu Lys Arg Ile Phe Glu
1               5                   10                  15

Lys Tyr Ala Ala Lys Glu Gly Asp Pro Asp Gln Leu Ser Lys Asp Glu
                20                  25                  30

Leu Lys Leu Leu Ile Gln Ala Glu Phe Pro Cys Leu Leu Lys Gly Pro
            35                  40                  45

Asn Thr Leu Asp Asp Leu Phe Gln Glu Leu Asp Lys Asn Pro Ala Glu
        50                  55                  60

Leu Glu Val Glu Met Ala Thr Gln Leu Arg Arg Phe Gly Asp Lys Leu
65                  70                  75                  80

Asn Phe Arg Gln Lys Leu Leu
            85

<210> SEQ ID NO 9
<211> LENGTH: 119
<212> TYPE: PRT
<213> ORGANISM: Artificial Sequence
<220> FEATURE:
<223> OTHER INFORMATION: Chimeric Variant of human protein and a variant
      of a BH3 domain

<400> SEQUENCE: 9

His Met Glu Asp Ile Ile Arg Asn Ile Ala Arg His Leu Ala Gln Val
1               5                   10                  15

Gly Asp Ser Met Asp Arg Ser Ile Pro Pro Gly Phe Ser Ala Thr Asp
                20                  25                  30

```
Ser Phe Asp His Lys Phe Phe Gln Met Val Gly Leu Lys Lys Lys
        35              40                  45

Ser Ala Asp Asp Val Lys Lys Val Phe His Met Leu Asp Lys Asp Lys
50                  55                  60

Ser Gly Phe Ile Glu Glu Asp Glu Leu Gly Phe Ile Leu Lys Gly Phe
65              70                  75                  80

Cys Pro Asp Ala Arg Asp Leu Ser Ala Lys Glu Thr Lys Met Leu Met
                85                  90                  95

Ala Ala Gly Asp Lys Asp Gly Asp Gly Lys Ile Gly Val Asp Glu Phe
            100                 105                 110

Ser Thr Leu Val Ala Glu Ser
        115

<210> SEQ ID NO 10
<211> LENGTH: 119
<212> TYPE: PRT
<213> ORGANISM: Artificial Sequence
<220> FEATURE:
<223> OTHER INFORMATION: Chimeric Variant of human protein and a variant
      of a BH3 domain

<400> SEQUENCE: 10

His Met Ser Met Thr Asp Leu Leu Asn Ala Glu Asp Ile Lys Lys Ala
1               5                   10                  15

Val Gly Ala Phe Ser Ala Thr Asp Ser Phe Asp His Lys Lys Phe Phe
                20                  25                  30

Gln Met Val Gly Leu Lys Lys Lys Ser Ala Asp Val Lys Lys Val
            35                  40                  45

Phe His Met Leu Asp Lys Asp Lys Ser Gly Phe Ile Glu Glu Asp Glu
    50                  55                  60

Leu Gly Phe Ile Leu Lys Gly Phe Cys Pro Asp Ala Arg Asp Leu Ser
65                  70                  75                  80

Ala Lys Glu Thr Lys Met Leu Met Ala Ala Gly Asp Lys Asp Gly Glu
                85                  90                  95

Asp Ile Ile Arg Asn Ile Ala Arg His Leu Ala Gln Val Gly Asp Ser
            100                 105                 110

Met Asp Arg Ser Ile Pro Pro
        115
```

CALBINDIN AND BH3 DOMAIN CHIMERIC PROTEINS AND METHODS FOR USE

RELATED APPLICATION DATA

This application is a national stage application, filed under 35 U.S.C. § 371, of International Patent Application No. PCT/US15/19095, filed on Mar. 6, 2015, which claims the benefit of priority of U.S. Provisional Patent Application Ser. No. 61/949,345, filed Mar. 7, 2014, which is incorporated herein by reference.

The contents of the text file named "SequenceProDa_41660-4001US.txt", which was created on Jul. 19, 2018, and is 10,521 bytes in size, are hereby incorporated by reference in their entirety.

FIELD OF TECHNOLOGY

The present disclosure relates generally to therapeutic proteins and, more particularly, to proteins, e.g., chimeric proteins, having increased stability and to methods of use of therapeutic agents in the treatment of cancers and other diseases.

BACKGROUND

Cancer and other diseases affect humans on a daily basis. Cancer, in particular, is a disease that spreads throughout a host's body, due to cell apoptosis, until the host ultimately succumbs to the disease.

Various forms of treatments, ranging from invasive to minimally invasive, are currently used to treat these diseases. These treatments include surgery, chemotherapy, radiation therapy, targeted therapy, etc. However, these treatments often cause the patient to feel ill during treatment and, moreover, often fall short of completely eviscerating the disease from the human.

SUMMARY

The present disclosure provides proteins, e.g., chimeric proteins, with extended half-lives and prolonged effectiveness as administered therapeutic agents. An aspect of the present disclosure relates to a chimeric protein capable of inducing apoptosis in cells. The chimeric protein includes a first peptide that is part of a stable human protein, and a second peptide that is a BH3 domain of human BH3-only proteins, and which imparts stability upon the first peptide, thereby resulting in increased stability of the overall chimeric protein. The BH3 domain of BH3-only proteins is either Bim, Bid, Bad, Bik, Bmf, Hrk, Puma, or Noxia.

The chimeric protein may have an amino acid sequence identical to SEQ ID NO: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10, as disclosed herein. The first peptide may be part of Calbindin D9k, N-terminal Calmodulin, C-terminal Calmodulin, or Parvalbumin. Moreover, the chimeric protein may include a targeting moiety that targets the chimeric protein to a cell. The targeting moiety may be folate conjugated to the chimeric protein by either a disulfide linkage or a maleimide linkage. Additionally, the chimeric protein may include a modifying group, such as polyethylene glycol, that extends the half-life of the chimeric protein.

Another aspect of the present disclosure relates to a method of treating an individual with a chimeric protein to induce apoptosis of cells. The method includes administering, to the individual, a therapeutically effective amount of the chimeric protein. The chimeric protein includes a first peptide that is part of a stable human protein and a second peptide that is a BH3 domain of human BH3-only proteins. The first peptide is either Calbindin D9k, N-terminal Calmodulin, C-terminal Calmodulin, or Parvalbumin. The chimeric protein can have a targeting sequence.

The method may further include exposing the treatment target to radiation in addition to administration of the chimeric protein. Furthermore, oxaliplatin may be administered along with the chimeric protein. The chimeric protein may also have an amino acid sequence identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10, as disclosed herein. The chimeric protein may be administered within a pharmaceutically acceptable composition, and the pharmaceutically acceptable composition may include an imaging probe. The BH3 domain may be from one of the BH3-only proteins Bim, Bid, Bad, Bik, Bmf, Hrk, Puma, or Noxia. Moreover, the chimeric protein may include a folate conjugated thereto, with the folate being a targeting moiety that targets the chimeric protein to a cell. Additionally, the folate may be conjugated to the chimeric protein by either a disulfide linkage or a maleimide linkage. The chimeric protein may further include polyethylene glycol conjugated thereto, with the polyethylene glycol extending the half-life of the chimeric protein. The BH3 domain may also have a label conjugated thereto.

Definitions

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refer to compounds that have the same basic chemical structure as a naturally occurring amino acid, by way of example only, an alpha-carbon that is bound to a hydrogen, a carboxyl group, an amino group, and an R group. Such analogs may have modified R groups (by way of example, norleucine) or may have modified peptide backbones, while still retaining the same basic chemical structure as a naturally occurring amino acid. Non-limiting examples of amino acid analogs include homoserine, norleucine, methionine sulfoxide, and methionine methyl sulfonium.

The term "conservatively modified variants" applies to both natural and non-natural amino acid and natural and non-natural nucleic acid sequences, and combinations thereof. With respect to particular nucleic acid sequences, "conservatively modified variants" refers to those natural and non-natural nucleic acids which encode identical or essentially identical natural and non-natural amino acid sequences, or where the natural and non-natural nucleic acid does not encode a natural and non-natural amino acid sequence, to essentially identical sequences. By way of example, because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Thus by way of example every natural or non-natural nucleic acid sequence herein which encodes a natural or non-natural polypeptide also describes every possible silent variation of the natural or non-natural nucleic acid. One of skill will recognize that each codon in a natural or non-natural nucleic acid (except AUG, which is ordinarily the only codon for methionine, and TGG, which is ordinarily the only codon for tryptophan) can be modified to yield a functionally identical molecule. Accordingly, each silent variation of a natural and non-natural nucleic acid which encodes a natural and non-natural polypeptide is implicit in each described sequence.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. By way of example, an agent or a compound being administered includes, but is not limited to, a natural amino acid polypeptide, non-natural amino acid polypeptide, modified natural amino acid polypeptide, or modified non-amino acid polypeptide. Compositions containing such natural amino acid polypeptides, non-natural amino acid polypeptides, modified natural amino acid polypeptides, or modified non-natural amino acid polypeptides can be administered for prophylactic, enhancing, and/or therapeutic treatments. An appropriate "effective" amount in any individual case may be determined using techniques, such as a dose escalation study.

The term "cell or population of cells" as used herein refers to an isolated cell or plurality of cells excised from a tissue or grown in vitro by tissue culture techniques. Most particularly, a population of cells refers to cells in vivo in a tissue of an animal or human.

The term "contacting a cell or population of cells" as used herein refers to delivering a peptide or probe according to the present disclosure to an isolated or cultured cell or population of cells or administering the probe in a suitable pharmaceutically acceptable carrier to the target tissue of an animal or human. Administration may be, but is not limited to, intravenous delivery, intraperitoneal delivery, intramuscularly, subcutaneously, or by any other method known in the art. One advantageous method is to deliver directly into a blood vessel leading immediately into a target organ or tissue such as a pancreas, thereby reducing dilution of the probe in the general circulatory system.

The term "pharmaceutically acceptable carrier" as used herein refers to a diluent, adjuvant, excipient, or vehicle with which a heterodimeric probe of the disclosure is administered and which is approved by a regulatory agency of the federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable, or synthetic origin, such as peanut oil, soybean oil, mineral oil, sesame oil, and the like. The pharmaceutical carriers can be saline, gum acacia, gelatin, starch paste, talc, keratin, colloidal silica, urea, and the like. When administered to a patient, the heterodimeric probe and pharmaceutically acceptable carriers can be sterile. Water is a useful carrier when the heterodimeric probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol, and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "protein" as used herein refers to a large molecule composed of one or more chains of amino acids in a specific order. The order is determined by the base sequence of nucleotides in the gene coding for the protein. Proteins are required for the structure, function, and regulation of the body's cells, tissues, and organs. Each protein has a unique function.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "variant" refers to a peptide or polynucleotide that differs from a reference peptide or polynucleotide, but retains essential properties. A typical variant of a peptide differs in amino acid sequence from another, reference peptide. Generally, differences are limited so that the sequences of the reference peptide and the variant are closely similar overall and, in many regions, identical. A variant and reference peptide may differ in amino acid sequence by one or more modifications (e.g., substitutions, additions, and/or deletions). A variant of a peptide includes conservatively modified variants (e.g., conservative variant of about 75%, about 80%, about 85%, about 90%, about 95%, about 98%, and about 99% of the original sequence). A substituted or inserted amino acid residue may or may not be one encoded by the genetic code. A variant of a peptide may be naturally occurring, such as an allelic variant, or it may be a variant that is not known to occur naturally.

The term "target" as used herein refers to a peptide, cell, tissue, tumor, etc., for which it is desired to detect. The target peptide may be on a cell surface, the cell being isolated from an animal host, a cultured cell, or a cell or population of cells in a tissue of an animal.

The present disclosure includes peptides which are derivable from the naturally occurring sequence of the peptide. A peptide is said to be "derivable from a naturally occurring amino acid sequence" if it can be obtained by fragmenting a naturally occurring sequence, or if it can be synthesized based upon knowledge of the sequence of the naturally occurring amino acid sequence or of the genetic material (DNA or RNA) that encodes this sequence. Included within the scope of the present disclosure are those molecules which are said to be "derivatives" of a peptide. Such a "derivative" or "variant" shares substantial similarity with the peptide or a similarly sized fragment of the peptide and is capable of functioning with the same biological activity as the peptide.

A derivative of a peptide is said to share "substantial similarity" with the peptide if the amino acid sequences of the derivative is at least 80%, at least 90%, at least 95%, or the same as that of either the peptide or a fragment of the peptide having the same number of amino acid residues as the derivative.

The derivatives of the present disclosure include fragments which, in addition to containing a sequence that is substantially similar to that of a naturally occurring peptide may contain one or more additional amino acids at their amino and/or their carboxy termini. Similarly, the disclosure includes peptide fragments which, although containing a sequence that is substantially similar to that of a naturally occurring peptide, may lack one or more additional amino acids at their amino and/or their carboxy termini that are naturally found on the peptide.

The term "prophylactically effective amount," as used herein, refers an amount of a composition containing at least one non-natural amino acid polypeptide or at least one modified non-natural amino acid polypeptide prophylactically applied to a patient which will relieve to some extent one or more of the symptoms of a disease, condition, or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The phrase "substantially similar," in the context of two nucleic acids or polypeptides, refers to two or more sequences or subsequences that have at least 75%, preferably at least 85%, more preferably at least 90%, 95% or higher, or any integral value therebetween nucleotide or amino acid residue identity, when compared and aligned for maximum correspondence, as measured using a sequence comparison algorithm such as those described below for example, or by visual inspection. Preferably, the substantial identity exists over a region of the sequences that is at least about 10, preferably about 20, more preferable about 40-60 residues in length or any integral value therebetween, preferably over a longer region than 60-80 residues, more preferably at least about 90-100 residues, and most preferably the sequences are substantially identical over the full length of the sequences being compared, such as the coding region of a nucleotide sequence for example.

The term "synergistic", as used herein, refers to a combination of prophylactic or therapeutic effective agents which is more effective than the additive effects of any two or more single agents. A synergistic effect of a combination of prophylactic or therapeutic agents may permit the use of lower dosages of one or more of the agents and/or less frequent administration of the agents to a subject with a specific disease or condition. In some cases, a synergistic effect of a combination of prophylactic or therapeutic agents may be used to avoid or reduce adverse or unwanted side effects associated with the use of any single therapy.

The term "therapeutically effective amount," as used herein, refers to the amount of a composition containing at least one non-natural amino acid polypeptide and/or at least one modified non-natural amino acid polypeptide administered to a patient already suffering from a disease, condition, or disorder, sufficient to cure or at least partially arrest, or relieve to some extent one or more of the symptoms of the disease, disorder, or condition being treated. The effectiveness of such compositions depends upon conditions including, but not limited to, the severity and course of the disease, disorder, or condition, previous therapy, the patient's health status and response to the drugs, and the judgment of the treating physician. By way of example only, therapeutically effective amounts may be determined by routine experimentation, including but not limited to a dose escalation clinical trial.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with gene, cDNA, mRNA, oligonucleotide, and polynucleotide.

The disclosure also encompasses the obvious or trivial variants of the above-described fragments which have inconsequential amino acid substitutions (and thus have amino acid sequences which differ from that of the natural sequence) provided that such variants have an activity which is substantially identical to that of the above-described derivatives. Examples of obvious or trivial substitutions include the substitution of one basic residue for another (i.e., Arg for Lys), the substitution of one hydrophobic residue for another (i.e., Leu for Ile), or the substitution of one aromatic residue for another (i.e., Phe for Tyr), etc.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
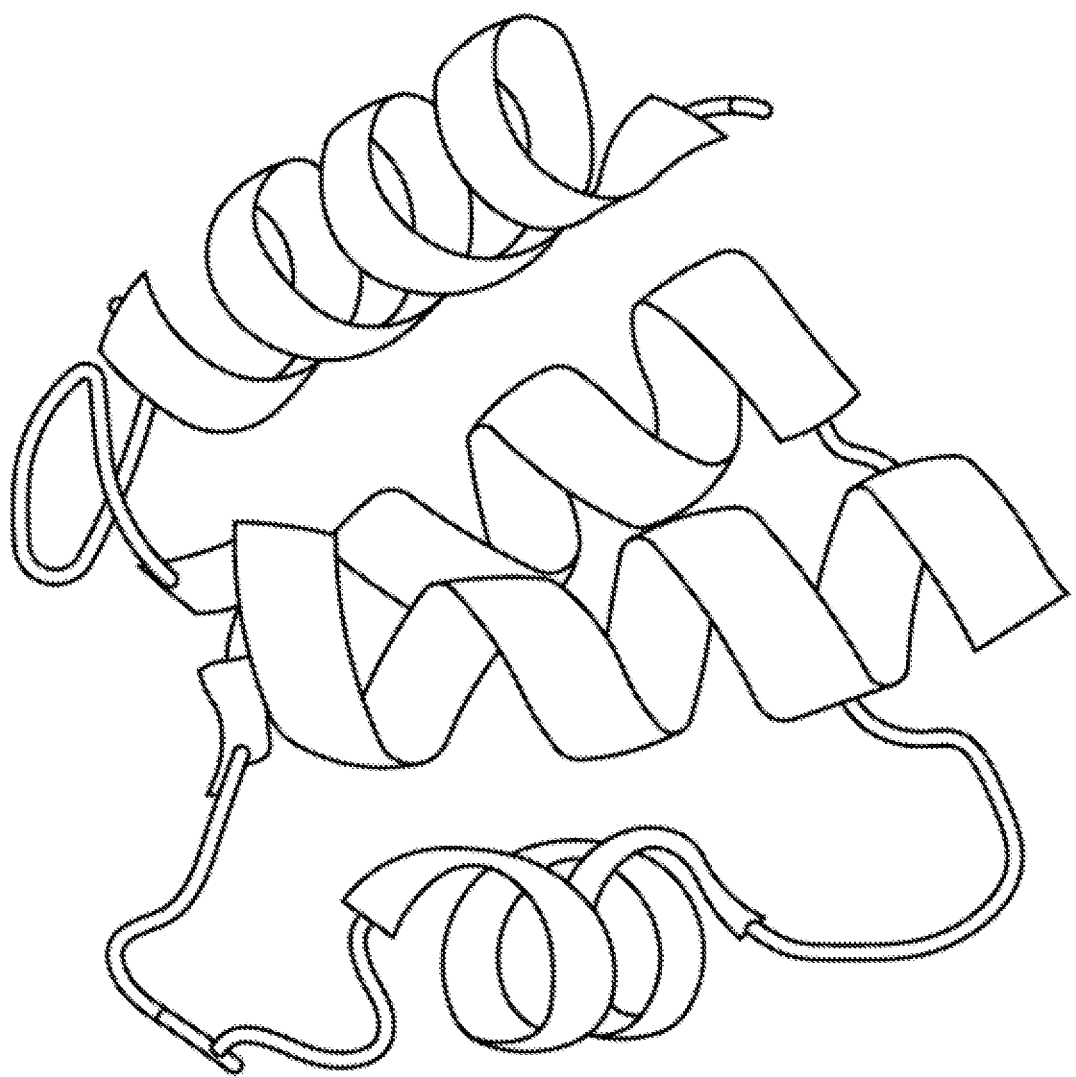
FIG. 1 is a rendering of a chimeric protein according to the present disclosure.
Figure 2:
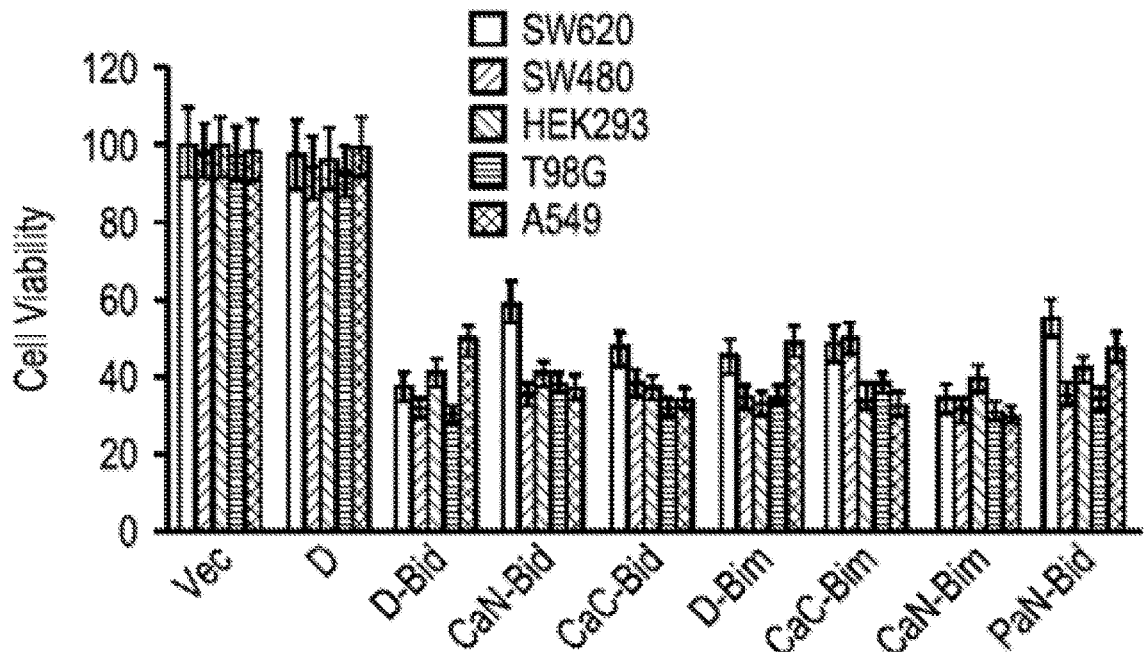
FIG. 2 is a graphical representation illustrating the effects of expression of different chimeric proteins in cells according to the present disclosure.
Figure 3:
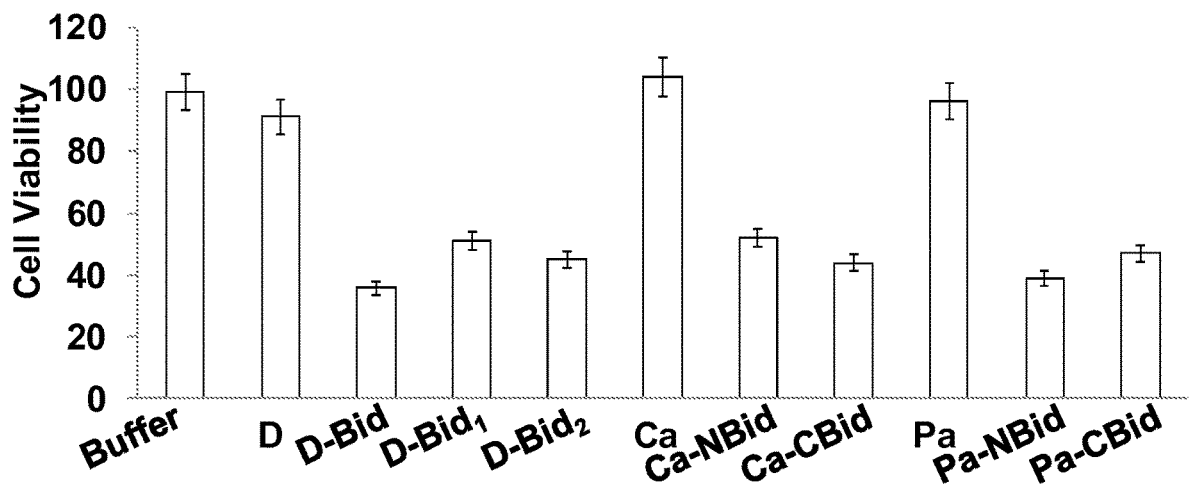
FIG. 3 is a graphical representation illustrating the effects of chimeric proteins having different host peptides and the BH3 domain of Bid on the apoptosis of SW620 cells according to the present disclosure.
Figure 4:
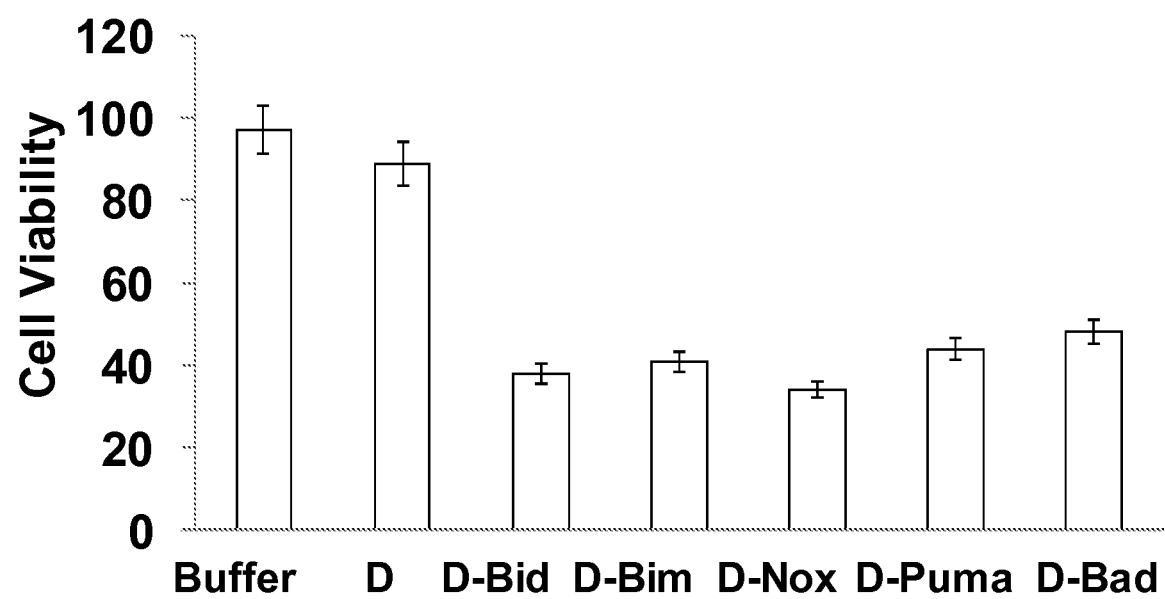
FIG. 4 is a graphical representation illustrating the effects of chimeric proteins having a Calbindin D9k host peptide and BH3 domains from different BH3-only proteins on the apoptosis of SW620 cells according to the present disclosure.
Figure 5:
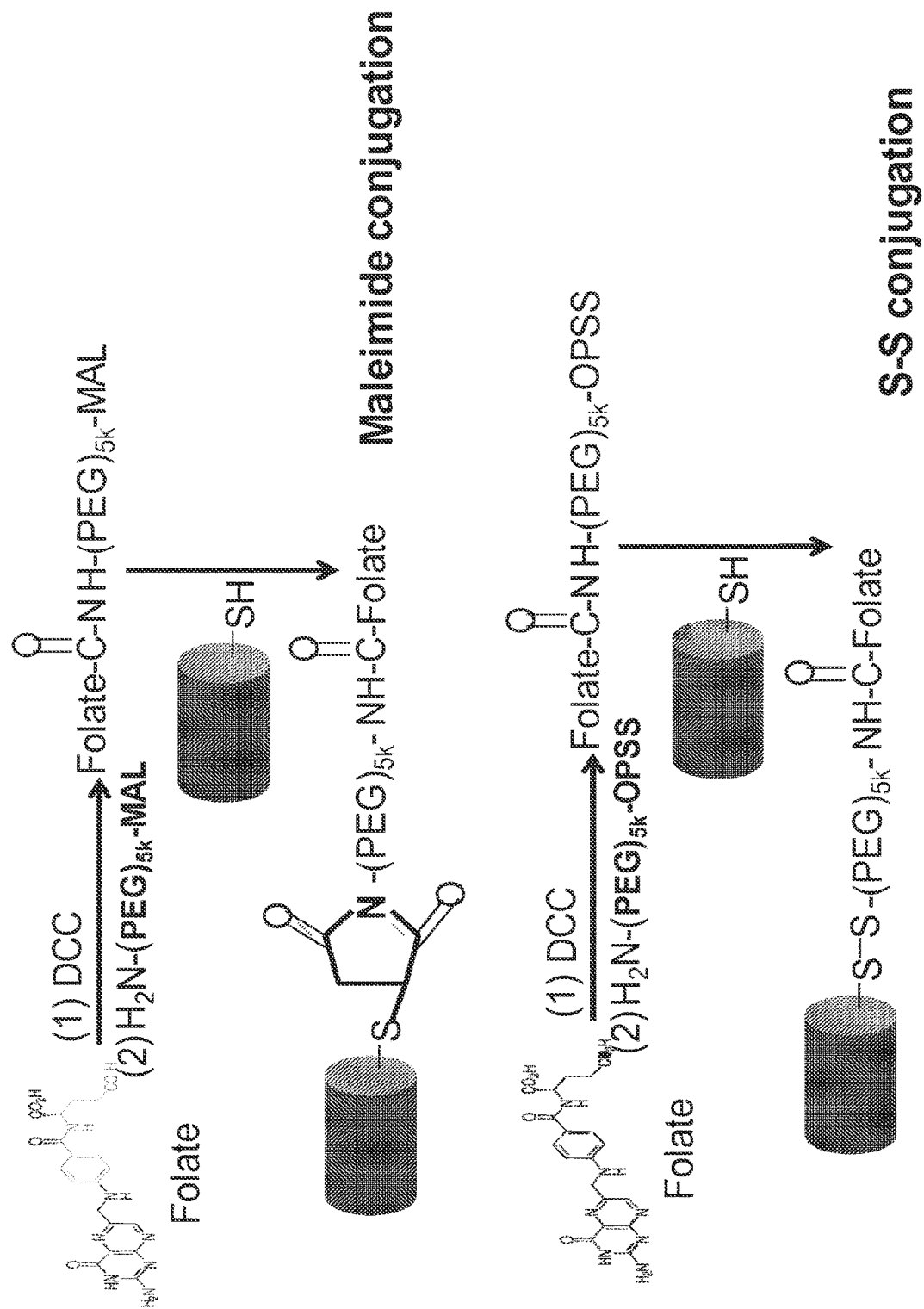
FIG. 5 illustrates conjugation of chimeric proteins to a folate according to the present disclosure.
Figure 6:
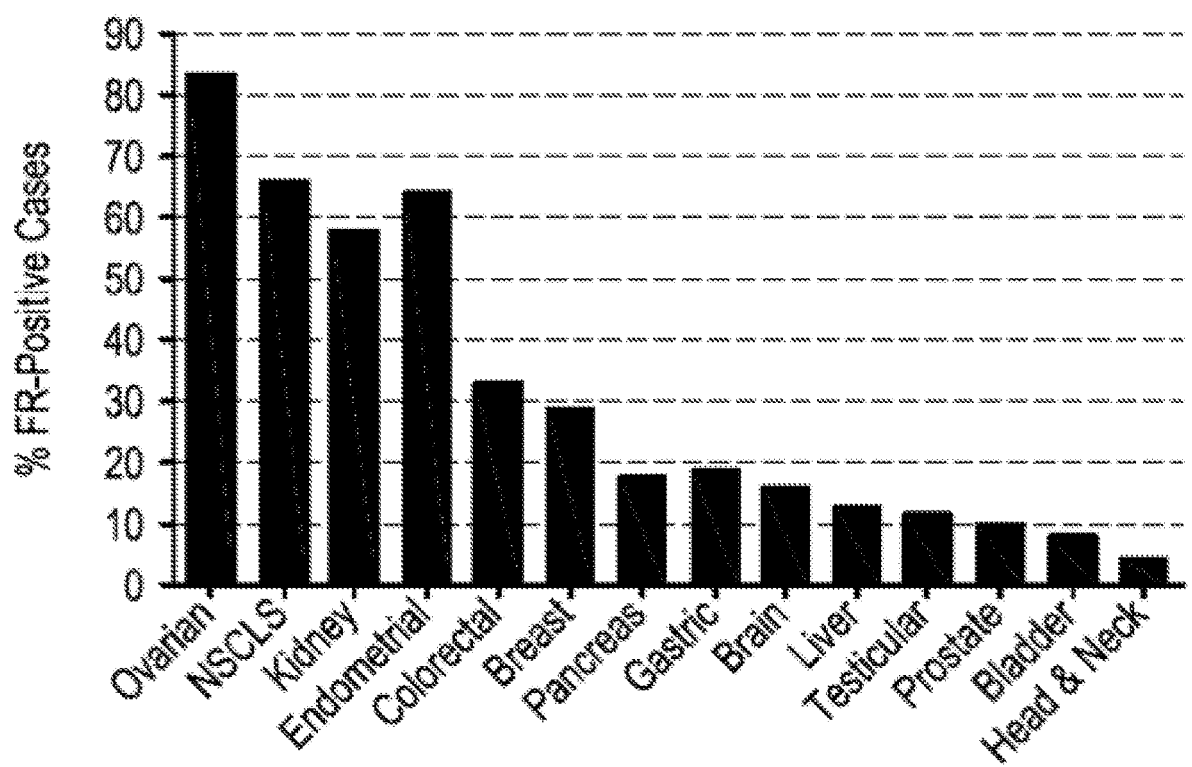
FIG. 6 is a graphical representation illustrating expression of folate receptors in cancers according to the present disclosure
Figure 7:
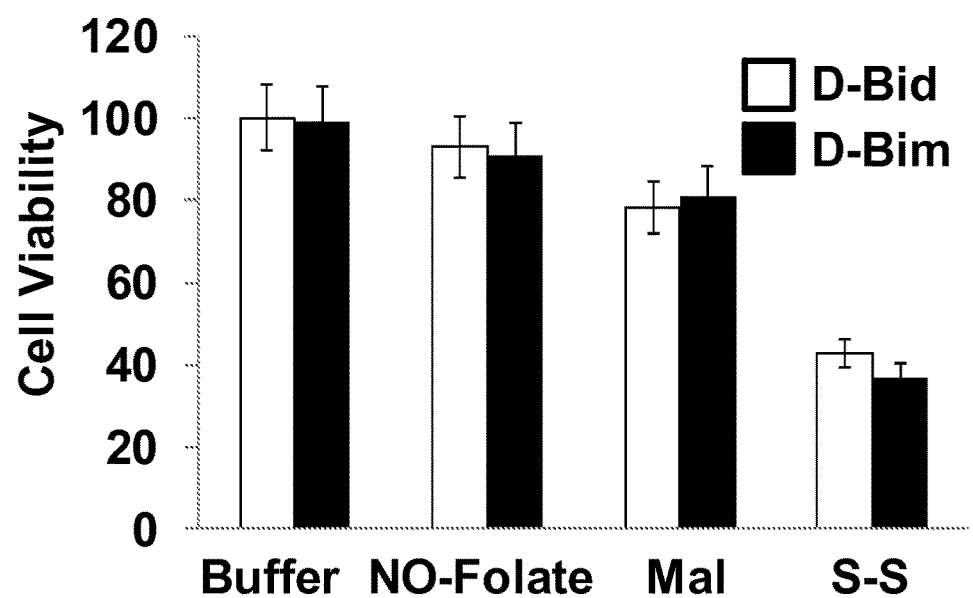
FIG. 7 is a graphical representation illustrating the effects of a chimeric protein with a Calbindin D9k host protein, a BH3 domain from Bid or Bim, and a conjugated folate on SW620 cells according to the present disclosure.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

Modifications and changes can be made in the structure of the peptides of this disclosure and still obtain a molecule having similar characteristics as the peptide (e.g., a conservative amino acid substitution). For example, certain amino acids can be substituted for other amino acids in a sequence without appreciable loss of activity. Because it is the interactive capacity and nature of a peptide that defines that peptide's biological functional activity, certain amino acid sequence substitutions can be made in a peptide sequence and nevertheless obtain a peptide with like properties.

In making such changes, the hydropathic index of amino acids can be considered. The importance of the hydropathic amino acid index in conferring interactive biologic function on a peptide is generally understood in the art. It is known that certain amino acids can be substituted for other amino acids having a similar hydropathic index or score and still result in a peptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of an amino acid determines the secondary structure of the resultant peptide, which in turn defines the interaction of the peptide with other molecules, such as enzymes, substrates, receptors, antibodies, antigens, and the like. It is known in the art that an amino acid can be substituted by another amino acid having a similar hydropathic index and still obtain a functionally equivalent peptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent peptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid can be substituted for another having a similar hydrophilicity value and still obtain a biologically equivalent, and in particular, an immunologically equivalent peptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser); (Arg: Lys); (Asn: Gln, His); (Asp: Glu, Cys, Ser); (Gln: Asn); (Glu: Asp); (Gly: Ala); (His: Asn, Gln); (Ile: Leu, Val); (Leu: Ile, Val); (Lys: Arg); (Met: Leu, Tyr); (Ser: Thr); (Thr: Ser); (Tip: Tyr); (Tyr: Trp, Phe); and (Val: Ile, Leu).

The terms "subject," "individual," "patient," and "host" are used interchangeably herein and refer to any vertebrate, particularly any mammal, and most particularly including human subjects, farm animals, and mammalian pets. The subject may be, but is not necessarily, under the care of a health care professional such as a doctor or veterinarian and may be in need of therapeutic treatment with the compositions of the disclosure.

The term "stability" as used herein refers to when a peptide essentially retains its physical and chemical stability and integrity upon storage and exposure to what would be inactivating conditions, including but not limited to, oxidation, heat denaturation, peptidase cleavage, and the like, and which would substantially reduce or eliminate the biological activity or structural integrity of the peptide compared to when the peptide has not been subject to such conditions.

The term "vector" as used herein means a DNA molecule serving as a vehicle capable of stably carrying exogenous genes into host cells. For useful application, a vector should be replicable, have a system for introducing itself into a host cell, and possess selectable markers.

The present disclosure generally provides proteins, particularly those in an in vivo environment, with extended half-lives and prolonged effectiveness as administered therapeutic agents. Each protein includes a first peptide linked to another, more stable second peptide, thereby forming a fusion peptide with the stability of the second peptide being conferred to the first peptide. For example, the first peptide may substitute for a domain of the second peptide such as an α-helix domain, while still retaining its biological activity.

FIG. 1 illustrates a chimeric protein having a first/host peptide linked to a second peptide, thereby forming a fused protein with stability of the second peptide being conferred to the first peptide. The protein may be an apoptosis-inducing agent, cancer therapeutic agent, and/or agent for inhibiting cancer metastasis.

The first/host peptide may be Calbindin D9k ("D"), a N-terminal or C-terminal half-domain of Calmodulin ("Ca"), Parvalbumin ("Pa"), an amino acid sequence variant thereof, or a modified variant thereof. Furthermore, the host peptide may be of human origin. The second peptide is a BH3 domain peptide of different BH3-only proteins such as, for example, Bim (DMRPEIWIAQELRRIGDEFNAYYAR) (Amino Acids 80-104 of SEQ ID NO: 1), Bid (EDIIRNIARHLAQVGDSMDRSIP) Amino Acids 80-103 of SEQ ID NO: 2), Bad (NLWAAQRYGRELRRMSDEFVDSFKK) (Amino Acids 62-86 of SEQ ID NO: 6), Puma (EEQWAREIGAQLRRMADDLNAQYER) Amino Acids 62-86 of SEQ ID NO: 7), and Noxia (PAELEVECATQLRRFGDKLNFRQKLL) Amino Acids 62-87 of SEQ ID NO: 8). The resulting grafted, or chimeric, protein retains biophysical/biochemical properties of the original protein without the BH3 domain attached thereto, and can induce apoptosis of cancerous cells or other cells. Moreover, the protein can contain conservative variants of the peptides explicitly disclosed herein.

In some instances, the second peptide of the chimeric protein may have the amino acid sequence of a BH3 domain and the first/host peptide may have an amino acid sequence that is part of a human protein (SEQ ID NO: 1-SEQ ID NO: 10), evidenced as follows:

D-Bim
(Sequence Id No. 1)
```
  1                         M S T K K S P E E
 21 L K R I F E K Y A A K E G D P D Q L S K
 41 D E L K L L I Q A E F P C L L K G P N T
 61 L D D L F Q E L D K N G A G A V S F E D
 81 M R P E I W I A Q E L R R I G D E F N A
101 Y Y A *
```

D-Bid
(Sequence Id No. 2)
```
  1                         M S T K K S P E E
 21 L K R I F E K Y A A K E G D P D Q L S K
 41 D E L K L L I Q A E F P C L L K G P N T
 61 L D D L F Q E L D K N G A G A V S F E E
 81 D I I R N I A R H L A Q V G D S M D R S
101 I W *
```

Ca-Bim
(Sequence Id No. 3)
```
  1                         M A D Q L T E E Q
 21 I A E F K E A F S L F D K D G D G T I T
 41 T K E L G T V M R S L G Q N P T E C E L
 61 Q D M I N E V D A A G N G T I A F P D M
 81 R P E I W I A Q E L R R I G D E F N A Y
101 Y A
```

Ca-Bid
(Sequence Id No. 4)
```
  1                         M A D Q L T E E Q
 21 I A E F K E A F S L F D K D G D G T I T
 41 T K E L G T V M R S L G Q N P T E C E L
 61 Q D M I N E V D A A G N G T I A F P E D
 81 I I R N I A R H L A Q V G D S M D R S I
101 W
```

D-Bim1
(Sequence Id No. 5)
```
  1 E L M H H H H H H L E M S T K K S P E E
 21 L K R I F E K Y A A K E G D P D Q L S K
 41 D E L K L L I Q A E F P C L L K G P N T
 61 L D D L F Q E L D K N G D G E V S F E E
 81 F Q V L V K K I A Q E L R R I G D E F N
101 A
```

D-Bad
(Sequence Id No. 6)
```
  1 H M S T K K S P E E L K R I F E K Y A A
 21 K E G D P D Q L S K D E L K L L I Q A E
 41 F P C L L K G P N T L D D L F Q E L D K
 61 N N L W A A Q R Y G R E L R R M S D E F
 81 V D S F K K
```

D-Puma
(Sequence Id No. 7)
```
  1 H M S T K K S P E E L K R I F E K Y A A
 21 K E G D P D Q L S K D E L K L L I Q A E
 41 F P C L L K G P N T L D D L F Q E L D K
```

-continued

```
 61 N E E Q W A R E I G A Q L R R M A D D L

81 N A Q Y E R

D-Nox
                                  (Sequence Id No. 8)
  1 H M S T K K S P E E L K R I F E K Y A A

21 K E G D P D Q L S K D E L K L L I Q A E

41 F P C L L K G P N T L D D L F Q E L D K

61 N P A E L E V E M A T Q L R R F G D K L

81 N F R Q K L L

PaN-Bid
                                  (Sequence Id No. 9)
  1 H M E D I I R N I A R H L A Q V G D S M

21 D R S I P P G F S A T D S F D H K K F F

41 Q M V G L K K K S A D D V K K V F H M L

61 D K D K S G F I E E D E L G F I L K G F

81 C P D A R D L S A K E T K M L M A A G D

101 K D G D K I G V D E F S T L V A E S

PaC-Bid
                                 (Sequence Id No. 10)
  1 H M S M T D L L N A E D I K K A V G A F

21 S A T D S F D H K K F F Q M V G L K K K

41 S A D D V K K V F H M L D K D K S G F I

61 E E D E L G F I L K G F C P D A R D L S

81 A K E T K M L M A A G D K D G E D I I R

101 N I A R H L A Q V G D S M D R S I P P
```

A segment of an α-helix in the host protein having a length, i.e., a number of residues, similar to that of a selected BH3 domain is identified, and a replacement site is located in the loop adjacent to the selected α-helix segment. The BH3 domain sequence replaces a portion of the selected loop, i.e., a few amino acids of the loop are replaced by the end sequence of the BH3 domain. The resultant chimeric protein constructs may be computer simulated by web-based protein structure modeling/prediction programs to find the best construes based on, for example, stability and surface exposure of the BH3 domain.

The chimeric protein or chimeric nanoparticle includes a protein with various functionalities by combining a BH3 domain variant and a host protein based on a genetic engineering and a protein engineering technique. For example, the BH3 domain peptide may be grafted into a stable human host protein, e.g., Calbindin D9k, Calmodulin Half Domain, or Human Parvalbumin, and the grafting of the BH3 domain peptide into a stable host protein would stabilize the secondary structure of the peptide and the entire protein. In another example, a Calbindin D9k host protein, or a portion thereof, includes a BH3 peptide. The BH3 peptide was grafted into the Calbindin D9k host protein by replacing a C-terminal helix. A protein agent according to the present disclosure may therefore be used to treat cancer and be targeted to specific cancer cells. For instance, a chimeric protein having a BH3 peptide can induce apoptosis of a target cell, e.g., a cancer cell.

FIG. 2 illustrates the effects of expression of different chimeric proteins in cells. All the BH3 domains tested were effective in inducing cell apoptosis when expressed in the cells. The indicated proteins were expressed in the indicated cells. Expression levels were confirmed by immunoblots using antibodies against individual host proteins. Cell viability was measured by cell counting 48 hours after exogenous expression of the indicated proteins. Vector ("Vec") expression cells were used as a reference (100% cell viability). The error bars indicate standard deviations across five repeating experiments.

FIG. 3 illustrates the effects of chimeric proteins having different host peptides and the BH3 domain of Bid on the apoptosis of SW620 cells. As indicated, Calbindin D9k was the most effective host peptide in inducing apoptosis. The SW620 cells were treated with 5 μM of the indicated proteins. The proteins were conjugated to folate by a disulfide bond via a 5 kDa PEG. Cell viability was measured by cell counting 48 hours after treatment with the indicated proteins. Buffer treated cells were used as a reference (100% cell viability). The error bars indicate standard deviations across five repeating experiments.

FIG. 4 illustrates the effects of chimeric proteins having a Calbindin D9k host peptide and different BH3 domains on the apoptosis of SW620 cells. As indicated, the chimeric protein containing the BH3 domain of Noxia ("Nox") was the most effective in inducing apoptosis. The SW620 cells were treated with 5 μM of the indicated proteins. The proteins were conjugated to folate by a disulfide bond via a 5 kDa PEG. Cell viability was measured by cell counting 48 hours after treatment with the indicated proteins. Buffer treated cells were used as a reference (100% viability). The error bars indicate standard deviations across five repeating experiments.

The chimeric protein may include a targeting moiety such as, for example, a folate. The use of a folate is beneficial in targeting the chimeric protein to cells having one or more folate receptors or cells expressing excessive amounts of folate receptors. The folate may be attached to the protein by a S-S bond, disulfide bridge, or another type of covalent linkage via, for example, a Cysteine residue. With a disulfide bond, the overall connectivity is R-S-S-R. The use of a disulfide bridge improves the delivery of the protein to target cells. A protein of the disclosure may exhibit 20-fold enhanced targeting ability. Conjugation of the chimeric protein to folate, as disclosed herein, is illustrated in FIG. 5. Other targeting moieties, include but are not limited to molecules interact with cell surface receptors and trigger endocytosis (e.g., gastrin-releasing peptide and its derivatives, somatostatin and its derivatives, such as Octreotide, Affibody for HER2, aptamer for various growth factor receptors, vasoactive intestinal peptide, and others.

FIG. 6 illustrates expression of folate receptors in cancers. Advanced and difficult-to-treat cancers overexpress folate receptors. Furthermore, folate receptor expression correlates with poor prognosis.

FIG. 7 illustrates the effects of a chimeric protein with a Calbindin D9k host protein, a Bid or Bim BH3 domain, and a conjugated folate on SW620 cells. The SW620 cells were treated with 5 μM of a chimeric protein (D-Bid (open bar) or D-Bim (filled bars)). The proteins were conjugated to folate by a di-sulfide (S-S) or maleimide (MAL) bond via a 5 kDa PEG. "NO-Folate" indicates the cells treated with proteins not containing a conjugated folate. Cell viability was measured by counting cells 48 hours after treatment with the indicated proteins. Buffer treated cells were used as a reference (100% viability). The error bars indicate standard deviations across five repeated experiments. As FIG. 7 evidences, the disulfide bonded conjugate produced the lowest cell viability, i.e., it had the greatest impact upon cell apoptosis.

Figure 8:
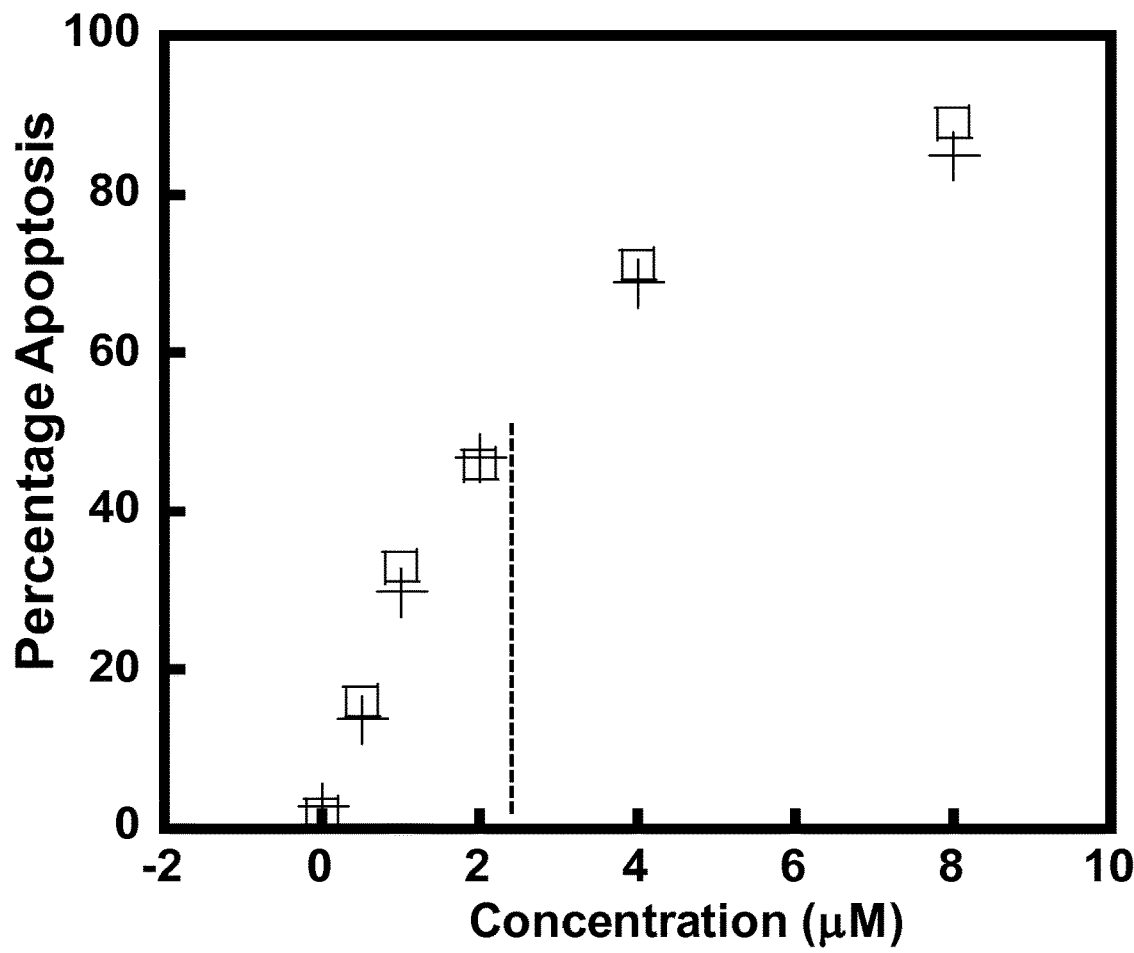
FIG. 8 is a graphical representation illustrating the treatment of SW620 cells with different concentrations of the chimeric protein D-Bid with a disulfide bonded (S-S) folate conjugate according to the present disclosure.

FIG. 8 illustrates the treatment of SW620 cells with different concentrations of the chimeric protein D-Bid with a disulfide bonded (S-S) folate conjugate. Cell apoptosis was measured 48 hours after the treatment by Tunnel staining using a Tunnel kit. Cell apoptosis was expressed as percentage apoptosis by counting positive stains vs total cell number (means of six counting) and normalized to that of the buffer treated cells. $EC_{50}$ is estimated at around 2.2 µM by 50% cell apoptosis under the treatment.

Figure 9:
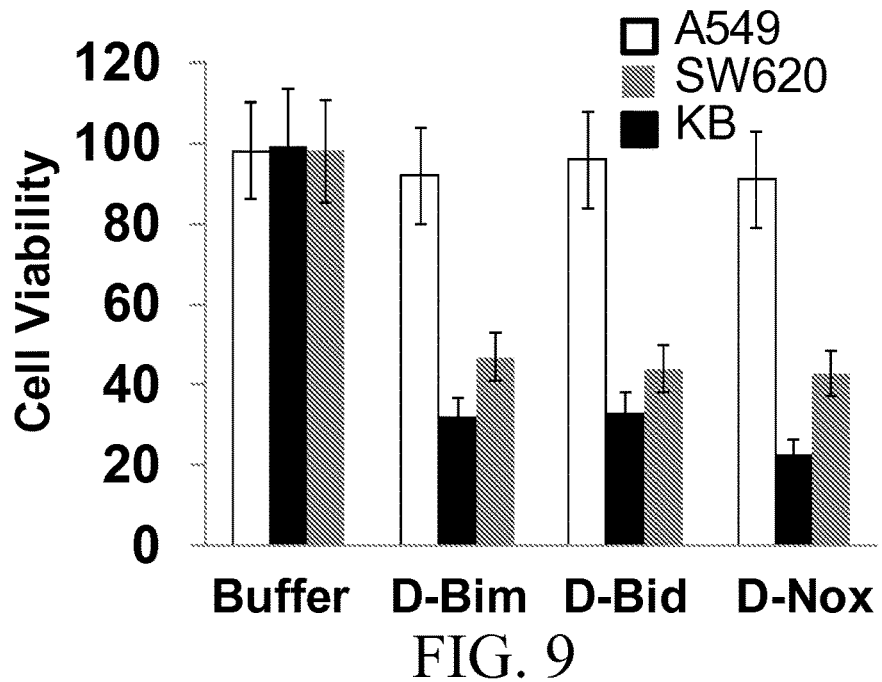
FIG. 9 is a graphical representation illustrating the effects of chimeric proteins with a Calbindin D9k host protein, BH3 domains from different BH3-only proteins, and a conjugated folate on A549, SW620, and KB cells according to the present disclosure.

FIG. 9 illustrates the effects of chimeric proteins with a Calbindin D9k host protein, different BH3 domains, and a conjugated folate on A549, SW620, and KB cells. As indicated, KB cells had high folate receptor levels, SW620 cells had medium folate receptor levels, and A549 cells had very low folate receptor levels. Furthermore, apoptosis induction has a strong folate receptor dependence. The A549, SW620, and KB cells were treated with 5 µM of the proteins. The proteins were conjugated to folate by a disulfide bond via a 5 Kda PEG. Cell viability was measured by cell counting 48 hours after treatment with the indicated proteins. Buffer treated cells were used as a reference (100% cell viability). The error bars indicate standard deviations across five repeating experiments.

Figure 10A:
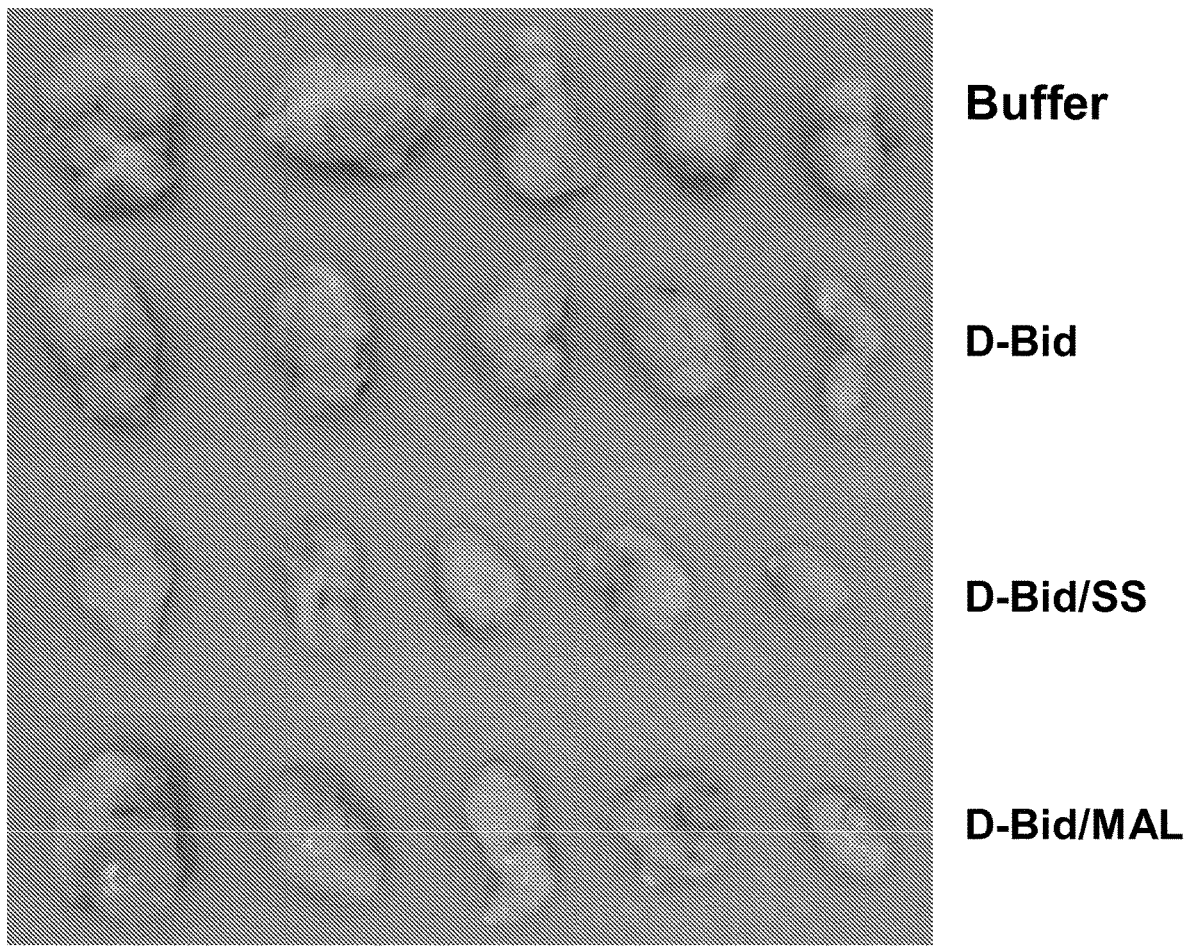
FIG. 10A illustrates the effects (end point tumor sizes) of chimeric proteins (D-Bid) with/without folate conjugation, or with disulfide bond (SS) or maleimide (Mal) conjugation on xenograft tumor of SW620 cells according to the present disclosure.
Figure 10B:
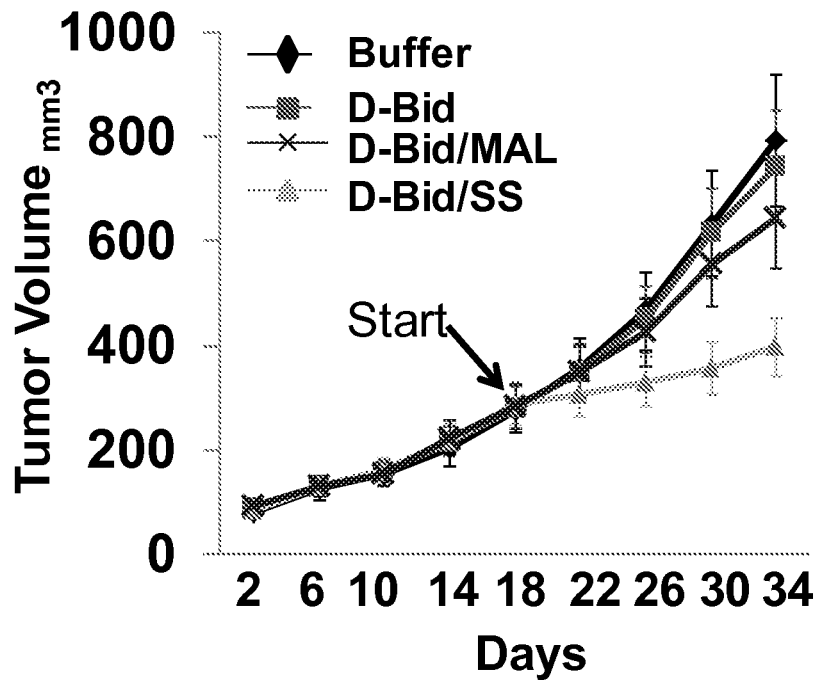
FIG. 10B is a graphical representation illustrating the effects (tumor growth curve) of chimeric protein (D-Bid) with/without folate conjugation, or with disulfide bond (SS) or maleimide (Mal) conjugation on xenograft tumor of SW620 cells according to the present disclosure.
Figure 10C:
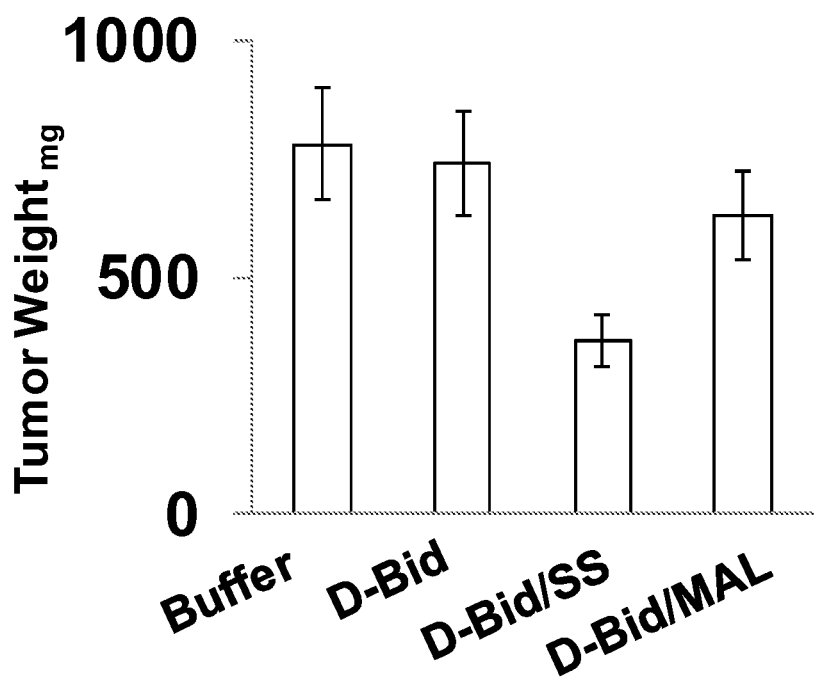
FIG. 10C a graphical representation illustrating the effects (end point tumor weight) of chimeric protein (D-Bid) with/without folate conjugation, or with disulfide bond (SS) or maleimide (Mal) conjugation on xenograft tumor of SW620 cells according to the present disclosure.

FIGS. 10A, 10B, and 10C illustrate the effects of folate conjugated chimeric proteins on SW620 cells. SW620 cells ($1 \times 10^7$) were inoculated in a nude mouse. At 18 days after inoculation, tumor growth was measured at around 290 mm$^3$. The mice were then treated with daily doses of 10 mg/kg of the indicated proteins via i.p. injection. These daily treatments were stopped after 11 days. All mice were killed 32 days after tumor inoculation. The tumors were sliced out and weighed. Tumor volumes were measured and calculated by:

Tumor Volume=Π/6×(width)$^2$×length

D-Bid is the protein with a folate conjugate, D-Bid/SS is the protein with a disulfide bonded folate conjugate, and D-Bid/MAL is the protein with a maleimide bonded folate conjugate. The error bars indicate standard deviations across five mice.

Figure 11A:
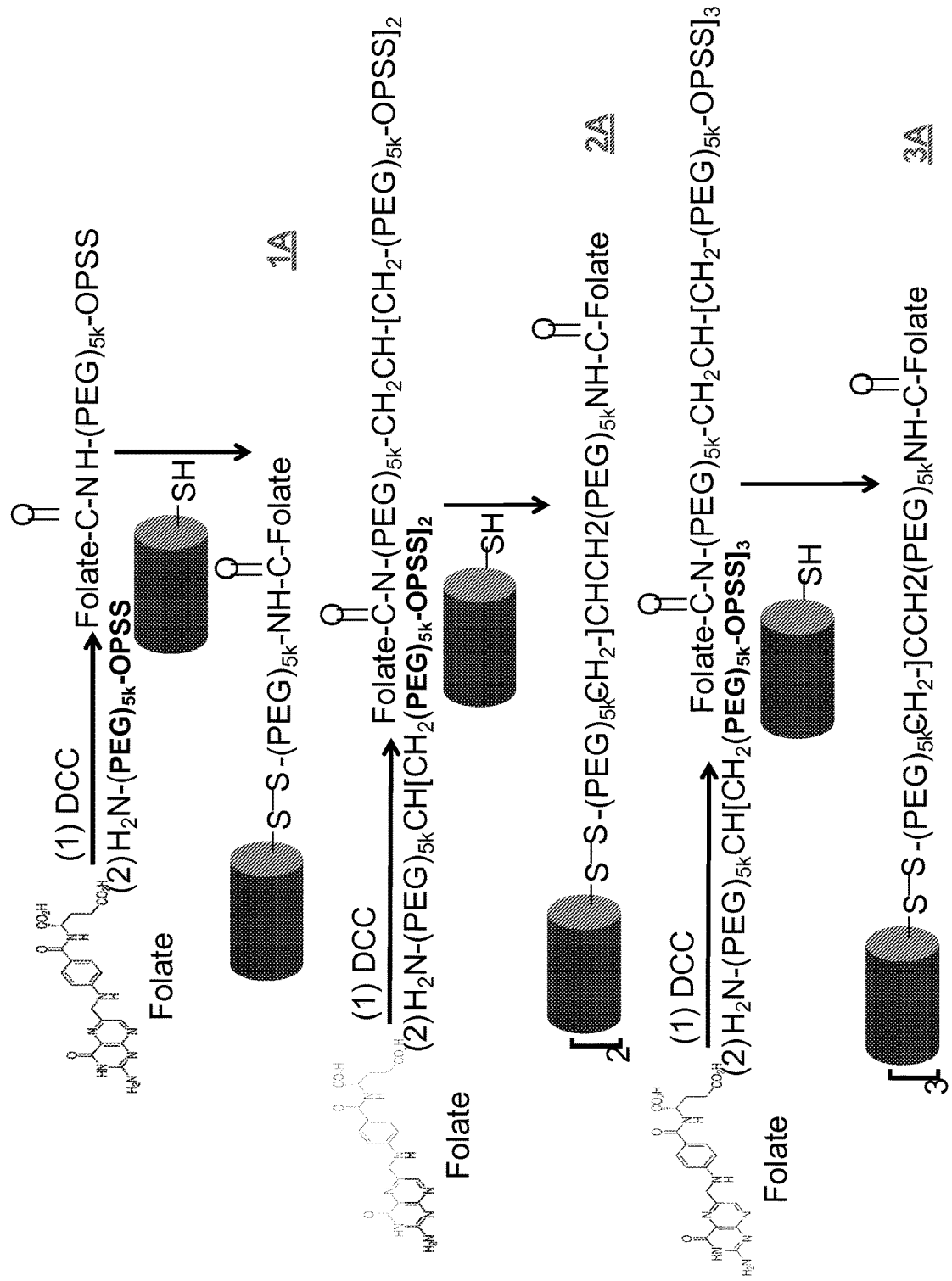
FIG. 11A illustrates conjugation of multi-arm PEGylation agents to a chimeric protein according to the present disclosure.
Figure 11B:
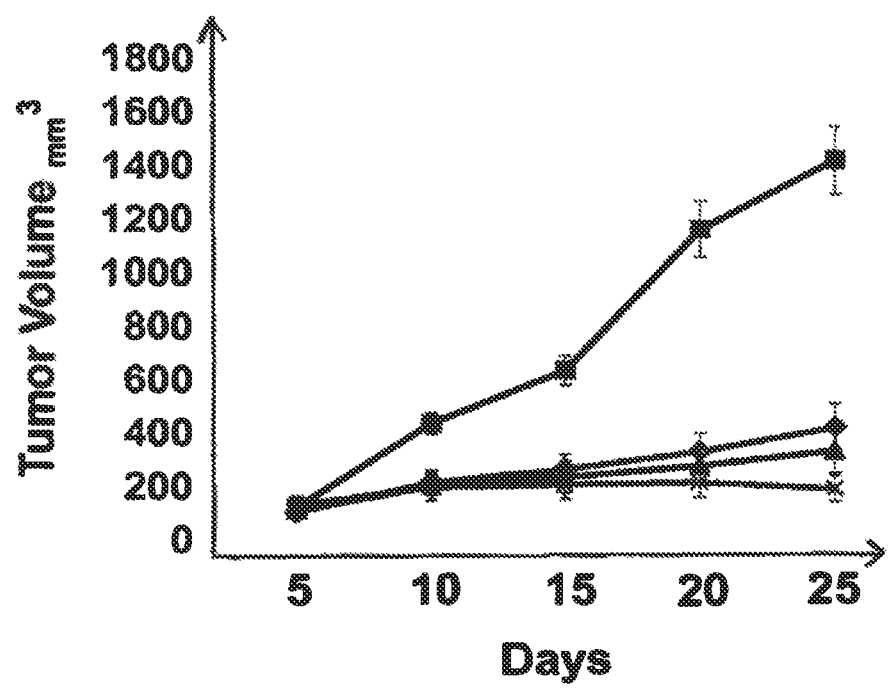
FIG. 11B is a graphical representation illustrating the effects (tumor growth curve) of a single folic acid conjugated to different numbers of chimeric protein D-Nox by a multi-arm PEGylation agent according to the present disclosure.
Figure 12:
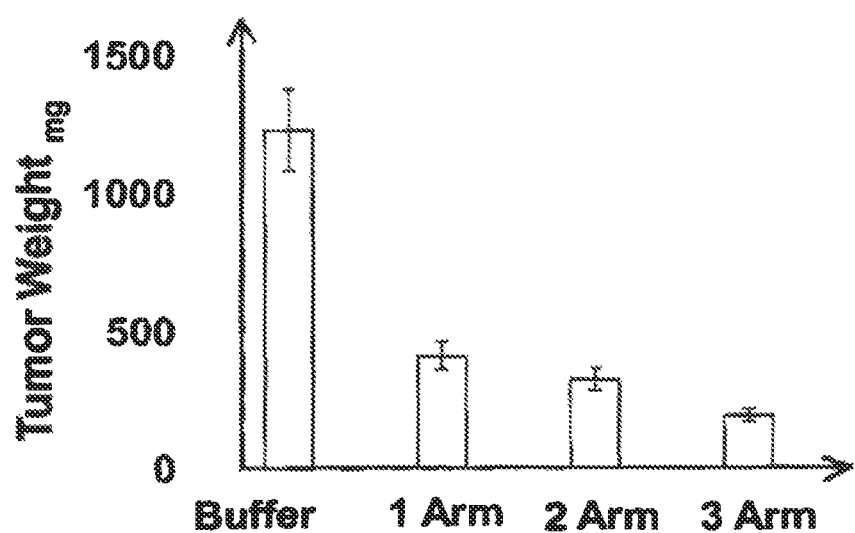
FIG. 12 is a graphical representation illustrating the effects (endpoint tumor weight) of a single folic acid conjugated to different numbers of chimeric protein D-Nox by a multi-arm PEGylation agent according to the present disclosure.

FIG. 11A illustrates various multi-arm PEGylation agents. FIGS. 11B (tumor growth curve) and 12 (endpoint tumor weight) illustrate the effects of folate conjugation to varying numbers of chimeric protein D-Nox by a multi-arm PEGylation agent on SW620 cells. Treatment of the xenograft SW620 cells (6 mice/group) was initiated 5 days after tumor inoculation. Treatment consisted of 10 mg/kg (measured by protein D-Nox) i.p. administrations, with one dose being administered every other day for a total of 10 doses. D-Nox 1 Arm, 2 Arm, and 3 Arm denote the conjugation of one folic acid to 1, 2, and 3 D-Nox proteins respectively. The error bars indicate standard deviations across 6 mice.

Figure 13:
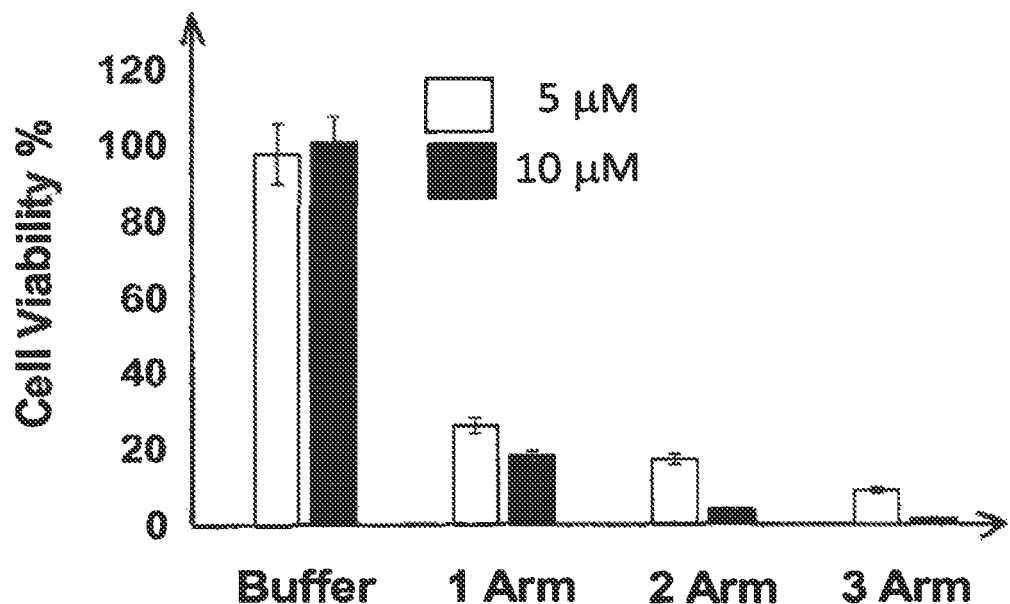
FIG. 13 is a graphic representation illustrating the effects of a single folic acid conjugated to different numbers of chimeric protein D-Nox by a multi-arm PEGylation agent according to the present disclosure.

FIG. 13 illustrates the effects of folate conjugation to varying numbers of chimeric protein (D-Nox by a multi-arm PEGylation agent) on SW620 cells. The SW620 cells were treated with 5 µM (open bars) or 10 µM (filled bars) of the chimeric protein (measured by protein D-Nox) D-Nox 1 Arm, 2 Arm, 3 Arm, or buffer. 1 Arm, 2 Arm, and 3 Arm denote the conjugation of one folic acid to 1, 2, or 3 D-Nox proteins respectively by S-S bonds. Cell viability was measured by staining and is represented as percentage of treated cells.

The protein may be modified to extend, even further, their half-lives by conjugating a modifying group such as, for example, polyethylene glycol ("PEG") to the chimeric protein. Conjugation of the modifying group may include identifying a residue or residues that can be substituted by Cys and to provide an attachment site for the modifying group.

Furthermore, a label may be attached to the second peptide of the chimeric protein.

When administering the chimeric protein to a subject animal or human, the subject animal or human may receive an effective dose of the chimeric protein in conjunction with a pharmaceutically acceptable carrier, thereby resulting in a pharmaceutically acceptable composition. The pharmaceutically acceptable composition may include an imaging probe.

The chimeric protein may function as an inducible apoptosis system to provide a universal cell ablation system for use in mammalian cells and organisms that allow the study of the biological function of selected cells or a cell type in the mammalian body and thereby the creation of a wide range of animal models of human diseases. Such an inducible apoptosis system is beneficial for all applications requiring its universal activation in any organ and any cell type of the mammalian body, including the brain. It is to be noted that the non-human transgenic animal can be used to study the function of cells, e.g., in mice, by inducible apoptosis. For this purpose, the coding region of the recombinant or chimeric proteins may be combined with suitable sequences, for example a cell type specific promoter region, and the protein transgene may be inserted into the mouse germline by pronuclear injection or other methods known in the art.

The protein according to the present disclosure may be co-administered with another form of therapy. When referring to the treatment of cancer, the term "co-administering" and derivatives thereof as used herein means either simultaneous administration or any manner of separate sequential administration of an agent other than the protein agent, as described herein, and at least one chemotherapeutic agent and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. If the administration is not simultaneous, the compounds are administered in a close time proximity to each other. Furthermore, it does not matter if the compounds are administered in the same dosage form, e.g., one compound may be administered topically and another compound may be administered orally.

Figure 14:
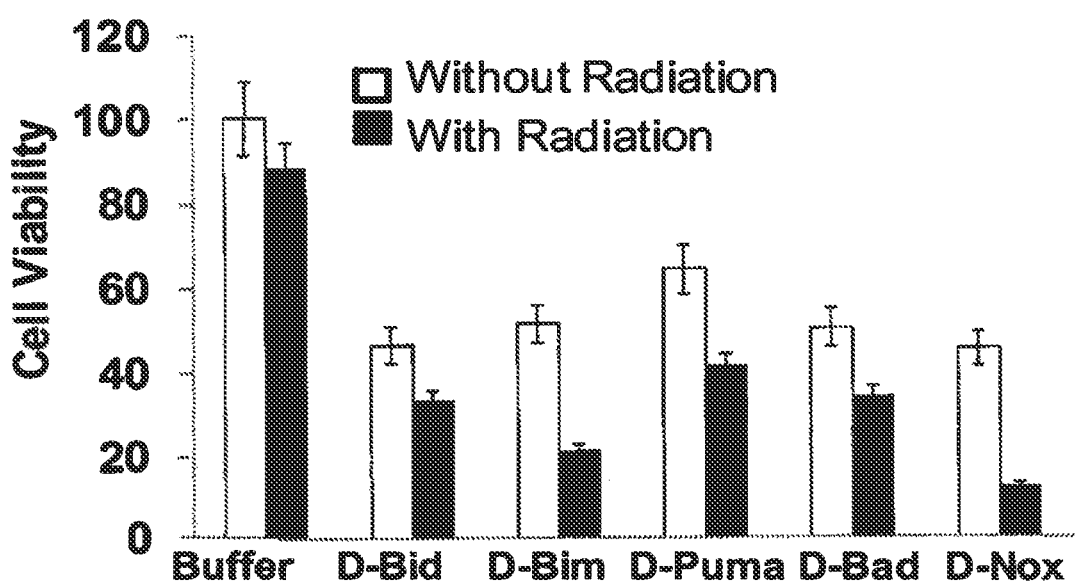
FIG. 14 is a graphical representation illustrating the synergistic effect of radiation therapy with chimeric proteins including a Calbindin D9k host peptide and a BH3 domain of different BH3-only proteins on SW620 cells according to the present disclosure.

FIG. 14 illustrates the synergistic effect of radiation therapy with chimeric proteins including a Calbindin D9k host peptide and different BH3 domains on SW620 cells. The SW620 cells were treated with 5 µM of the indicated proteins for 1 hour. The cells were then irradiated, with radiation, by 10 Gray (filled bars) or without radiation (open bars). Cell viability was measured by cell counting 24 hours after the radiation treatments were started. Buffer treated without radiation cells were used as a reference (100% viability). The error bars indicate standard deviations across five repeating experiments.

Figure 15:
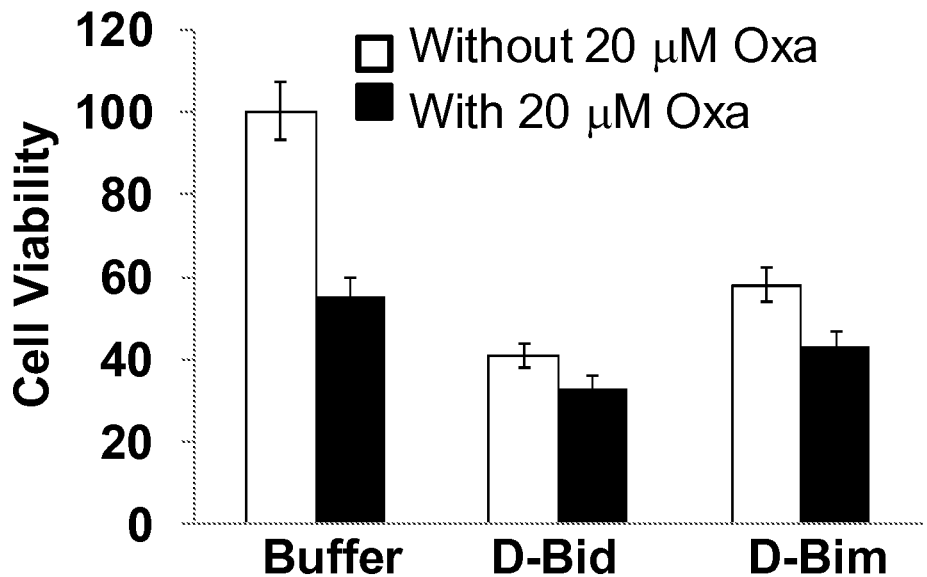
FIG. 15 is a graphical representation illustrating the synergist effect of oxaliplatin with chimeric proteins including a Calbindin D9k host peptide and a BH3 domain of different BH3-only proteins on SW620 cells according to the present disclosure.

FIG. 15 illustrates the synergist effect of oxaliplatin with chimeric proteins including a Calbindin D9k host peptide and different BH3 domains on SW620 cells. The SW620 cells were treated with 5 µM of the indicated proteins and with (filled bars) or without (open bars) 20 µM of oxaliplatin. Cell viability was measured by cell counting 48 hours after treatment with the indicated proteins. Buffer treated without oxaliplatin cells were used as a reference (100% viability). The error bars indicate standard deviations across five repeating experiments.

Figure 16:
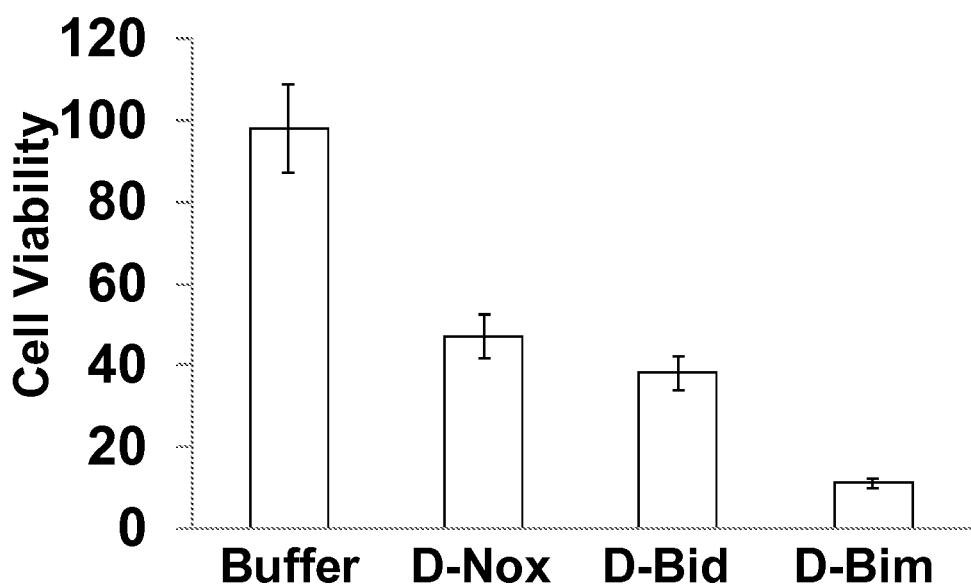
FIG. 16 is a graphical representation illustrating the treatment of Raw264.7 cells, i.e., macrophage cells, with chimeric proteins including a Calbindin D9k host peptide and a BH3 domain of different BH3-only proteins according to the present disclosure.

The therapeutic protein may be used to treat Inflammatory Diseases such as rheumatoid arthritis, which is mediated by induction of macrophage apoptosis. FIG. 16 illustrates the treatment of Raw264.7 cells, i.e., macrophage cells, with chimeric proteins including a Calbindin D9k host peptide and different BH3 domains. As indicated, the chimeric proteins were effective in inducing apoptosis of activated macrophage cells. The Raw264.7 cells were treated with 5 µM of the indicated proteins, which were conjugated to folate via a S-S bond. Cell viability was measured by cell counting 48 hours after treatment with the indicated proteins. Buffer treated cells were used as a reference (100% viability). The error bars indicate standard deviations across five repeating experiments.

Treatment may be accomplished with varying doses as well as dosing regimens, provided the combination of the doses is effective at treating any one or more of a number of therapeutic parameters. These treatment regimens may alternatively or may also be based on doses and dosing schedules that maximize therapeutic effects, such as those described herein. A dose of the protein may not be therapeutically effective when administered individually, but may be therapeutically effective when administered in combination with another agent. Thus, the therapeutically effective dose of a combination of the protein and a therapeutically radioactive isotope may comprise doses of individual active agents that, when administered alone, would not be therapeutically effective or would be less therapeutically effective than when administered in combination with each other.

The target cell of the chimeric protein may be an isolated cell. Furthermore, the target cell may be in a tissue of a subject animal or human. An imaging probe may be administered to the subject animal or human as a pharmaceutically acceptable composition. The binding site of the chimeric protein to the target cell may be a receptor on the surface of the cell through an attached targeting moiety.

Another aspect of the disclosure relates to a method for inducing apoptosis of a cell expressing a chimeric protein according to the disclosure. The method includes transfection of DNA encoding the chimeric proteins capable of inducing apoptosis of the cell.

The specific examples disclosed herein are to be construed as merely illustrative, and not limitative of the remainder of the disclosure in any way whatsoever. Without further elaboration, it is believed that one skilled in the art can, based on the description herein, utilize the present disclosure to its fullest extent.

The disclosed examples are put forth so as to provide those of ordinary skill in the art with a complete disclosure and description of how to perform the methods and use the compositions and compounds disclosed and claimed herein. Efforts have been made to ensure accuracy with respect to numbers e.g., amounts, temperature, etc., but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations, e.g., 1%, 2%, 3%, and 4%, and the sub-ranges, e.g., 0.5%, 1.1%, 2.2%, 3.3%, and 4.4%, within the indicated range. The term "about" can include ±1%, ±2%, 3%, ±4%, 5%, ±6%, 7%, ±8%, ±9%, or ±10%, or more of the numerical value(s) being modified.

What is claimed is:

1. A chimeric protein capable of inducing apoptosis in cells, comprising:
   a first peptide is Calbindin D9k; and
   a second peptide is a BH domain of BH3 domain of a BH3-only protein, the BH3 domain is one of BH3-only proteins Bim, Bid, Bad, Puma, or Noxia, wherein a C-terminal helix of the first peptide is replaced with the BH3 domain that is grafted into the first peptide.

2. The chimeric protein of claim 1, wherein
   the chimeric protein has an amino acid sequence selected from the group consisting of SEQ ID NO: 1, SEQ ID NO:2, SEQ ID NO:5, SEQ ID NO:6, SEQ ID NO:7, SEQ ID NO:8.

3. The chimeric protein of claim 1, further comprising: a targeting moiety conjugated to the chimeric protein.

4. The chimeric protein of claim 3, wherein the targeting moiety is a folate.

5. The chimeric protein of claim 4, wherein the folate is conjugated to the chimeric protein by a disulfide linkage.

6. The chimeric protein of claim 4, wherein the folate is conjugated to the chimeric protein by a maleimide linkage.

7. The chimeric protein of claim 1, further comprising: a modifying group is conjugated to the chimeric protein; and the modifying group extends the half-life of the chimeric protein.

8. The chimeric protein of claim 7, wherein the modifying group is polyethylene glycol.

* * * * *